United States Patent [19]

Milliman

[11] Patent Number: 5,472,843
[45] Date of Patent: Dec. 5, 1995

[54] NUCLEIC ACID PROBES TO *HAEMOPHILUS INFLUENZAE* +B

[75] Inventor: Curt L. Milliman, St. Louis, Mo.

[73] Assignee: Gen-Probe Incorporated, San Diego, Calif.

[21] Appl. No.: 221,968

[22] Filed: Apr. 1, 1994

Related U.S. Application Data

[63] Continuation of Ser. No. 690,788, Apr. 25, 1991, abandoned.

[51] Int. Cl.[6] .............................. C12Q 1/68; C12N 15/11
[52] U.S. Cl. .............................................. 435/6; 536/24.32
[58] Field of Search .................. 435/6, 252.3; 536/23.7, 536/24.32

[56] References Cited

U.S. PATENT DOCUMENTS

| | | | |
|---|---|---|---|
| 4,689,295 | 8/1987 | Taber et al. | 435/6 |
| 5,030,557 | 7/1991 | Hogan et al. | 435/6 |

FOREIGN PATENT DOCUMENTS

| | | | |
|---|---|---|---|
| 31387/84 | 2/1985 | Australia | C07G 17/00 |
| 0133671 | 3/1985 | European Pat. Off. | C12Q 1/68 |
| 0155359 | 9/1985 | European Pat. Off. | C12Q 1/68 |
| 0232085 | 8/1987 | European Pat. Off. | C12Q 1/68 |
| 0245129 | 11/1987 | European Pat. Off. | C07H 21/04 |
| 0250662 | 1/1988 | European Pat. Off. | C12Q 1/68 |
| 0277237 | 8/1988 | European Pat. Off. | C12Q 1/68 |
| WO8301073 | 3/1983 | WIPO | C12P 19/34 |
| WO84/02721 | 7/1984 | WIPO | C12Q 1/68 |
| WO88/03957 | 6/1988 | WIPO | C12Q 1/68 |

OTHER PUBLICATIONS

Lane et al., 82 Proc. Natl. Acad. Sci. USA 6955, 1985.
Rogers et al., 82 Proc. Natl. Acad. Sci. USA 1160, 1985.
Brosius et al., 75 Proc. Natl. Acad. Sci., USA 4801, 1978.
Brosius et al., 77 Proc. Natl. Acad. Sci., USA 201, 1980.
Weisburg et al., 167 Journal of Bacteriology 570, 1986.
Kohne, American Clinical Products Review, Nov. 1986.
Razin, 49 Microbiological Reviews 419, 1985.
Crosa et al., 83 Journal of General Microbiology 271, 1974.
9 Clinical Microbiology Newsletter 90, 1987.
Stahl, 4 Biotechnology 623, 1986.
Brenner et al., 90 Annals of Internal Medicine 656, 1979.
Ludwig and Stackebrandt, 135 Archives of Microbiology 45, 1983.
Brenner et al., 1 Current Microbiology 71, 1978.
Bergey's Manual, 283–285, 1984.
Brenner et al., 35 International Journal of Systematic Bacteriology 50, 1985.
Grimont et al., 21 J. Clin. Microbiol. 431, 1985.
Brenner et al., 30 Internatonal Journal SB 236, 1980.
1 Bergy's Manual of Systematic Bacteriology 160, 1984.
Festl et al., 52 Applied and Environmental Microbiology 1190, 1986.
Carbon et al., 9 Nucleic Acid Research 2325, 1981.
Colwell et al., 24 International Journal of Systematic Bacteriology 422, 1974.
Brenner, 23 International Journal of Systematic Bacteriology 298, 1973.
Brenner, 1 Bergy's Manual of Systematic Bacteriology 408, 1984, McCarroll et al., 22 Biochemistry 5858, 1983.
Veldman et al., 9 Nucleic Acids Research 6935, 1981.
Kilpper–Balz et al., 7 Current Microbiology 245, 1982.
Kilpper–Balz and Schleifer, 10 FEMS Microbiology Letters 357, 1981.
Schleifer and Kilpper–Balz, 34 International Journal of Systematic Bacteriology 31, 1984.
Harvey and Greenwood, 33 International Journal of Systematic Bacteriology 275, 1983.
Lau et al., 447 System Appl. Microbiol. 1987.
Baess 91 Adv. Path. Microbiol. Immunol. Scand. Sect. B 201, 1983.
Imaeda, 35 International Journal of Systematic Bacteriology 147, 1985.
Baess and Bentzon, 86 Acta Pat. Microbiol. Scand. Sect. B 71, 1978.
Drake et al., 25 Journal Clinical Microbiology, 1987.
Stackebrandt and Schleifer, in Biological Biochemical, Biochemical Aspects of Actinomycetes 485, 1984.
Goodfellow and Minnikin, In The Mycobacteria, Kubica and Wayne, eds. Dekker, 1984.
Mordarski et al., 118 Journal of General Microbiology 313, 1980.
Goodfellow and Wayne, in 1 The Biology of the *Mycobacteria* 476, 1982.
Baess, 90 Acta Path. Microbiol. Immunol. Scand. Sect. B. 371, 1982.
Bradley, 113 Journal of Bacteriology 645, 1973.
Rogers et al., 82 Proc. Natl. Acad. Sci. USA 1160, 1985.
Yogev and Razin, 36 International Journal of Systematic Bacteriology 426, 1986.
Razin et al., 135 Ann. Microbiol. 9, 1984.
Gobel et al., 133 Journal of General Microbiology 1969, 1987.
Gobel, 226 Science 1211, 1984.
Razin, 49 Microbiol. Rev. 437, 1985.
Jones and Collins, Bergy's Manual of Systematic Bacteriology 1261, 1986.
Boddinghaus et al., 28 J. Clin. Micro 1751, 1990 (incomplete copy).
Rogall et al., 40 Int. J. Sys. Bact. 323, 1990 (incomplete copy).
Rogall et al., 13 J. Gen. Micro. 1915, 1990 (incomplete copy).
Stahl and Urbance 172 J. Bact. 116, 1990 (incomplete copy).
Kilian 93 J. Gen. Micro. 9, 1976 (incomplete copy).
Musser et al., 52 Inf. Imm. 183, 1986 (incomplete copy).
Malouin et al., 26 J. Clin. Micro. 2132, 1988.

*Primary Examiner*—Mindy B. Fleisher
*Assistant Examiner*—James Ketter
*Attorney, Agent, or Firm*—Lyon & Lyon

[57] ABSTRACT

This invention discloses hybridization assay probes for *Haemophilus influenzae* comprised of an oligonucleotide of about 14 to 18 nucleotides. These probes hybridize to variable regions of the 16S rRNA gene of *Haemophilus influenzae*. The oligonucleotide probes are complementary to the rRNA variable region of the rRNA gene. Such probe specificity offers a rapid, non-subjective method of identification and quantitation of a bacterial colony for the presence of selected rRNA sequences capable of distinguishing all strains of *Haemophilus influenzae*.

19 Claims, No Drawings

NUCLEIC ACID PROBES TO *HAEMOPHILUS INFLUENZAE*

This application is a continuation of application Ser. No. 07/690,788, filed Apr. 25, 1991, now abandoned.

FIELD OF THE INVENTION

The inventions described and claimed herein relate to the design and construction of nucleic acid probes to *Haemophilus influenzae* which are capable of detecting said organism in test samples of, e.g., sputum, urine, blood and tissue sections, food, soil and water.

INCORPORATION BY REFERENCE OF RELATED PATENTS & APPLICATIONS

The following applications are incorporated by reference in their entirety together with all other application cited herein:
1) U.S. Patent No. 4,851,330 to Kohne, entitled "Method For Detection, Identification and quantitation of non-viral organisms" issued Jul. 25, 1989;
2) EPO Patent Application No. PCT/US87/03009 to Hogan et. al., entitled "Nucleic Acid Probes for Detection and/or Quantitation of Non-Viral Organisms," International Publication Number WO 88/03957, Published Jun. 2, 1988.
3) U.S. application Ser. No. 816,711 entitled "Accelerated Nucleic Acid Reassociation Method," filed Jan. 7, 1986, abandoned in favor of U.S. application Ser. No. 644,879 filed Jan. 23, 1991; and
4) U.S. application Ser. No. 841,860 entitled "Method for Releasing RNA and DNA from Cells," filed Mar. 20, 1986, abandoned in favor of U.S. application Ser. No. 298,765 filed Jan. 17, 1989.
5) U.S. application Ser. No. 613,603 entitled "Homogeneous Protection Assay" filed Nov. 8, 1990.
6) EPO Application No. PCT/US88/03361 entitled "Acridinium Ester Labeling and Purification of Nucleotide Probes" filed Oct. 5, 1988.
7) U.S. application Ser. No. 124,975 entitled "Means and Methods for Enhancing Nucleic Acid Hybridization," allowed Dec. 17, 1990, filed Nov. 24, 1987.

BACKGROUND

Two single strands of deoxyribo-("DNA") or ribo("RNA") nucleic acid, comprised of nucleotides (adenine, cytosine, thymidine, guanine, uracil, inosine, etc.), may associate ("hybridize") to form a double helical structure in which the two polynucleotide chains running in opposite directions are held together by hydrogen bonds (a weak form of chemical bond) between pairs of matched, centrally located compounds known as "bases." Generally, in the double helical structure of nucleic acids, the base adenine (A) is hydrogen bonded to the base thymine (T) or uracil (U) while the base guanine (G) is hydrogen bonded to the base cytosine (C). At any point along the chain, therefore, one may find the classical "Watson-Crick" base pairs AT or AU, TA or UA, GC, or CG. One may also find AG, GU and other "wobble" or mismatched base pairs in addition to the traditional ("canonical") base pairs. Assuming that a first single strand of nucleic acid is sufficiently complementary to a second and that the two are brought together under conditions which will promote their hybridization, double stranded nucleic acid will result. Under appropriate conditions, DNA/DNA, RNA/DNA, or RNA/RNA hybrids may be formed.

A probe may be a single strand nucleic acid sequence which is complementary in some particular degree to the nucleic acid sequences sought to be detected ("target sequences"). It may also be labelled with a detectable moiety such as a radio-isotope, antigen or chemiluminescent moiety. A background description of the use of nucleic acid hybridization as a procedure for the detection of particular nucleic acid sequences is described in U.S. Pat. No. 4,851,330 to Kohne and entitled "Method for Detection, Identification and Quantitation of Non-Viral Organisms," issued Jul. 25, 1989 and in EPO Application No. PCT/US87/03009 to Hogan et al., entitled "Nucleic Acid Probes for Detection and/Or Quantitation of Non-Viral Organisms."

Also described in the Kohne patent and the Hogan et al. application are methods for determining the presence of RNA-containing organisms in a sample which might contain such organisms. These methods require the mixture of nucleic acids from a sample and a probe comprised of nucleic acid molecules which are shorter than the ribosomal-RNA ("rRNA") subunit sequence from which it was derived. The probes are sufficiently complementary to hybridize to the rRNA of one or more non-viral organisms or groups of non-viral organisms. The mixture is then incubated under specified hybridization conditions, and assayed for hybridization of the probe and any test sample rRNA.

Further, the Hogan et al. application describes numerous probes which detect only specifically targeted rRNA subunit subsequences in particular organisms or groups of organisms in a sample, even in the presence of many non-related organisms, or in the presence of closest known phylogenetic neighbors. The Hogan et al. application discloses hybridization assay probes for *Mycobacterium avium, Mycobacterium intracellulare, Mycobacterium tuberculosis, Mycobacterium africanum, Mycobacterium bovis, Mycobacterium microti*, the genus Mycobacterium, *Mycoplasma pneumoniae*, the genus Legionella, *Chlamydia trachomatis*, the genus Campylobacter, Enteroccocus, the genus Pseudomonas group I, *Enterobacter cloacae, Proteus mirabilis*, the genus Salmonella, *Escherichia coli*, bacteria, fungi, and *Neisseria gonorrhoeae*. Such probe sequences do not cross react with nucleic acids from the groups listed above, or any other bacterial species or infectious agent, under proper stringency.

This invention discloses and claims novel probes for the detection of *Haemophilus influenzae*. These probes are capable of distinguishing between *Haemophilus influenzae* and its known closest phylogenetic neighbors.

SUMMARY OF THE INVENTION

We have discovered and describe herein novel probes to *Haemophilus influenzae*. These probes which detect unique rRNA and rRNA gene sequences may be used in an assay for the detection and/or quantitation of *Haemophilus influenzae*.

Particularly, this invention discloses hybridization assay probes for *Haemophilus influenzae* comprised of an oligonucleotide of about 14 to 18 nucleotides. These probes hybridize to variable regions of the 16S rRNA gene unique to *Haemophilus influenzae*. The oligonucleotide probes are substantially complementary to the rRNA variable region of the rRNA gene. Such probe specificity offers a rapid, non-subjective method of identification and quantitation of a bacterial colony for the presence of specific rRNA sequences unique to all strains of *Haemophilus influenzae*.

DEFINITIONS

The following terms, as used in this disclosure and claims, are defined as:

nucleotide: a subunit of a nucleic acid consisting of a phosphate group, a 5-carbon sugar and a nitrogen containing base. In RNA the 5-carbon sugar is ribose. In DNA, it is a 2-deoxyribose. For a 5'-nucleotide the sugar contains a hydroxyl group (—OH) at the carbon-5. The term also includes analogs of such subunits.

nucleotide polymer: at least two nucleotides linked by phosphodiester bonds or analogs thereof. When greater than two nucleotides, such nucleotides could be contiguous or a combination of nucleotide and non-nucleotide units.

non-nucleotide unit: unit which does not significantly participate in hybridization of a polymer. Such units must not, for example, participate in any significant hydrogen bonding with a nucleotide, and would exclude units having as a component one of the five nucleotide bases or analogs thereof.

oligonucleotide: a nucleotide polymer generally about 10 to about 100 nucleotides in length, but which may be greater than 100 or shorter than 10 nucleotides in length.

nucleic acid probe: a single stranded nucleic acid sequence that will combine with a complementary single stranded target nucleic acid sequence to form a double-stranded molecule (hybrid). A nucleic acid probe may be an oligonucleotide or a nucleotide polymer. As a probe it will usually contain a detectable moiety which may be attached to the end(s) of the probe or may be internal to the sequence of the probe. The nucleotides which combine with the target nucleic acid need not be strictly contiguous as may be the case with a detectable moiety internal to the sequence of the probe.

detectable moiety: A molecule attached to, or synthesized as part of, a nucleic acid probe. This molecule should be uniquely detectable and will allow the probe to be detected as a result. These detectable moieties are often radioisotopes, chemiluminescent molecules, enzymes, haptens, or even unique oligonucleotide sequences.

hybrid: the complex formed between two single stranded nucleic acid sequences by Watson-Crick base pairings or non-canonical base pairings between the complementary bases.

hybridization: the process by which two complementary strands of nucleic acids combine to form double stranded molecules ("hybrids").

complementarity: a property conferred by the base sequence of a single strand of DNA or RNA which may form a hybrid or double stranded DNA:DNA, RNA:RNA or DNA:RNA through hydrogen bonding between Watson-Crick base pairs on the respective strands. Adenine (A) usually complements thymine (T) or Uracil (U), while guanine (G) usually complements cytosine (C).

mismatch: Any pairing, in a hybrid, of two nucleotides which do not form canonical Watson-Crick hydrogen bonds. In addition, for the purposes of the following discussions, a mismatch can include an insertion or deletion in one strand of the hybrid, relative to the other, which results in an unpaired nucleotide(s).

stringency: term used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

probe specificity: characteristic of a probe which describes its ability to distinguish between target and non-target sequences. Probe specificity is dependent on sequence and assay conditions and may be absolute (i.e., probe able to distinguish between target organisms and any nontarget organisms), or it may be functional (i.e., probe able to distinguish between the target organism and any other organism normally present in a particular sample). Many probe sequences can be used for either broad or narrow specificity depending on the conditions of use.

variable region: nucleotide polymer which differs by at least one base between the target organism and non-target organisms contained in a sample.

conserved region: a region which is not variable.

bacteria: members of the phylogenetic group eubacteria, which is considered one of the three primary kingdoms.

sequence divergence: process by which nucleotide polymers become less similar during evolution.

sequence convergence: Process by which nucleotide polymers become more similar during evolution.

Tm: temperature at which 50% of the probe is converted from the hybridized to the unhybridized form.

DESCRIPTION OF THE INVENTION

We have discovered DNA probes complementary to a particular rRNA sequence obtained from *Haemophilus influenzae*. Furthermore, we have successfully used those probes in a specific assay for the detection of *Haemophilus influenzae*, distinguishing *H. influenzae* from its known, most closely related taxonomic or phylogenetic neighbors.

With the exception of viruses, all prokaryotic organisms contain rRNA genes encoding 5S rRNA, 16S rRNA, and a larger rRNA molecule known as 23S rRNA. Using methods known to those skilled in the art, we have identified variable regions of rRNA sequences from the 16S rRNA of *Haemophilus influenzae*. This included partially or fully sequencing the rRNA of *Haemophilus influenzae* and closely related phylogenetic neighbors, aligning the sequences to reveal areas of maximum homology and examining the alignment for regions with sequence variation.

With respect to sequencing the rRNA, complementary oligonucleotide primers of about 10–100 bases in length can be hybridized to conserved regions in purified rRNA that are specific to the 5S, 16S, or 23S subunits and extended with the enzyme reverse transcriptase. Chemical degradation or dideoxynucleotide-terminated sequencing reactions can be used to determine the nucleotide sequence of the extended product. Lane, D. J. et al., *Proc. Nat'l Acad. Sci. USA* 82, 6955–6959 (1985). In a less preferred method, genomic ribosomal RNA sequences may also be determined.

It is not always necessary to determine the entire nucleic acid sequence in order to obtain a probe sequence. Extension from any single oligonucleotide primer can yield up to 300–400 bases of sequence. When a single primer is used to partially sequence the rRNA of the target organism and organisms closely related to the target, an alignment can be made as outlined below. Plainly, if a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

After sequencing, the sequences are aligned to maximize homology. The rRNA molecule has a close relationship of secondary structure to function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be "aligned" based on the conserved primary sequence and also on the conserved secondary structure elements. Once sequences are aligned it is possible to find the regions in which the primary sequence is variable.

We have identified variable regions by comparative analysis of rRNA sequences both published in the literature and sequences which we have determined ourselves. Computers and computer programs which may be used or adapted for the purposes herein disclosed are commercially available. Since the sequence evolution at each of the variable regions (for example, spanning a minimum of 10 nucleotides) is, for the most part, divergent, not convergent, we can confidently design probes based on a few rRNA sequences which differ between the target organism and its phylogenetically closest relatives. We have seen sufficient variation between the target organism and the closest phylogenetic relative found in the same sample to design the probe of interest.

We have identified the following useful guidelines for designing probes with desired characteristics. Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe:target nucleic acid hybrid should be chosen to be compatible with the assay conditions. This may be accomplished by avoiding long A and T rich sequences, by terminating the hybrids with G:C base pairs and by designing the probe with an appropriate Tm. The beginning and end points of the probe should be chosen so that the length and % G and % C result in a Tm about 2°–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as ionic strength of the reaction mixture increases and that the thermal stability of hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

Second, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe:nontarget hybrids. In designing probes the differences in Tm should be as large as possible.

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-complementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intramolecular hybrids. By designing a probe so that a substantial portion of the sequence of interest is single stranded the rate and extent of hybridization may be greatly increased. If the target is the genomic sequence corresponding to the rRNA then it will naturally occur in a double stranded form, this is also the case with the product of the polymerase chain reaction (PCR). These double stranded targets are naturally inhibitory to hybridization with a probe. Finally, there can be intramolecular and intermolecular hybrids formed within a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone, A. D. et al., *Nucleic Acids Research* 12, 4051–4060 (1984). Other well-known methods for construction of synthetic oligonucleotides may, of course, be employed. 2 J. Sambrook, E. F. Fritsch and T. Maniatis, *Molecular Cloning* 11 (2d ed 1989). The current DNA synthesizers are capable of producing large amounts of nucleic acid.

Once synthesized, selected oligonucleotide probes may also be labelled by any of several well known methods. 2 J. Sambrook, E. F. Fritsch and T. Maniatis, *Molecular Cloning* 11 (2d ed. 1989). Useful labels include radioisotopes as well as non-radioactive reporting groups. Isotopic labels include $^3$H, $^{35}$S, $^{32}$P, $^{125}$I, Cobalt and $^{14}$C. Most methods of isotopic labelling involve the use of enzymes and include the known methods of nick translation, end labelling, second strand synthesis, and reverse transcription. When using radio-labelled probes, hybridization can be detected by autoradiography, scintillation counting, or gamma counting. The detection method selected will depend upon the hybridization conditions and the particular radio isotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

Following synthesis and purification of a particular oligonucleotide sequence, several procedures may be utilized to determine the acceptability of the final product. The first is polyacrylamide gel electrophoresis, which is used to determine size. 2 J. Sambrook, E. F. Fritsch and T. Maniatis, *Molecular Cloning*, 11.51 (2d ed 1989). Such procedures are known in the art. In addition to polyacrylamide gel electrophoresis, High Pressure Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., patent application Ser. No. 613,603 filed Nov. 8, 1990 entitled "Homogeneous Protection Assay."

For Tm measurement using a Hybridization Protection Assay the following technique is used. A Probe:target hybrid is formed in target excess in a lithium succinate buffered solution containing lithium lauryl sulfate. Aliquots of this "preformed" hybrid are diluted in the hybridization buffer and incubated for five minutes at various temperatures starting below that of the anticipated Tm (typically 55° C.) and increasing in 2-5 degree increments. This solution is then diluted with a mildly alkaline borate buffer and incubated at a lower temperature (for example 50° C.) for ten minutes. Under these conditions the acridinium ester attached to a single stranded probe is hydrolyzed while that attached to hybridized probe is relatively "protected". This is referred to as the hybridization protection assay ("HPA"). The amount of chemiluminescence remaining is proportional to the amount of hybrid and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which effect relative hybrid stability during thermal denaturation. 2 J. Sambrook, E. F. Fritsch and T. Maniatis, *Molecular Cloning*, 9.51 (2d ed 1989).

Rate of hybridization may be measured by determining the $C_0T_{1/2}$. The rate at which a probe hybridizes to its target is a measure of the thermal stability of the target secondary structure in the probe region. The standard measurement of hybridization rate is the $C_0T_{1/2}$ which has units (moles of nucleotide per liter)×(seconds). Expressed more simply it is the concentration of probe times the half-life of hybridization at that concentration. This value is determined by hybridizing various amounts of probe to a constant amount of hybrid for a fixed time. For example, 0.05 pmol of target is incubated with 0.0012, 0.025, 0.05, 0.1 and 0.2 pmol of probe for 30 minutes. The amount of hybrid after 30 minutes is measured by HPA as described in the Tm section. The signal is then plotted as a log of the percent of maximum Relative Light Units ("RLU") (from the highest probe concentration) versus probe concentration (moles of nucleotide per liter). RLU are a measurement of the quantity of photons emitted by the labelled-probe measured by the luminometer. The $C_0T_{1/2}$ is found graphically from the concentration corresponding to 50% of maximum hybridization multiplied by the hybridization time in seconds. These values range from $9.0\times10^{-6}$ to $9\times10^{-5}$ with the preferred values being less than $3.5\times10^{-5}$.

The following example sets forth synthetic probes complementary to a unique rRNA sequence, or the corresponding gene, from a target organism, *Haemophilus influenzae*, and its use in a hybridization assay.

Example 1

*Haemophilus influenzae* is one of the three leading causes of bacterial meningitis. Between 75–80% of all cases of bacterial meningitis in infants and children is caused by *Haemophilus influenzae* serotype b. *Haemophilus influenzae* serotype b causes acute epiglottitis, pneumonia, septic arthritis, cellulitis and pericarditis, which are potentially fatal diseases. Recently, nontypable strains of *H. influenzae* were recognized as important human pathogens responsible for a variety of infections in adults and children. *H. influenzae* forms a heterogeneous group divided into five biotypes. (Musser, J. M., et al. 1986. Infec. and Immun. 52:183–191; and Kilian, M. 1976 J. Gen. Microbiol. 93:9–62) Although other Haemophilus species cause infections in humans, *H. influenzae* is the most clinically significant species due to the incidence and severity of the diseases it causes.

Current methods for identification of *Haemophilus influenzae* rely on traditional physiological and biochemical methods. These include gram stain morphology, oxidase reaction, hemolytic activity on horse blood plates, the porphyrin test, and requirements for growth factor X (hemin) and V (NAD). Serological methods such as latex agglutination have been used to identify the typable strains of *Haemophilus influenzae*. The invention described herein offers a rapid, non-subjective method of identification of a bacterial colony for the presence of specific ribosomal RNA sequences that are unique to all serotypes and biotypes of *Haemophilus influenzae*.

Probes specific for *Haemophilus influenzae* were identified by sequencing with a primer complementary to a conserved region in the 16S rRNA. The following sequences were characterized and shown to be specific for *Haemophilus influenzae*, (SEQ ID NO: 1) 5'-GGC GCCAGAGT-TAAACCC-3' and (SEQ ID NO: 2) 5'-CGCAGCT-TCGCTTC-3'. The phylogenetically near neighbors *H. aphrophilus*, *H. ducreyi*, *H. haemolyticus*, *H. parahaemolyticus*, *H. parainfluenzae* and *H. paraphrophilus* were used as comparisons with the sequence of *H. influenzae*.

These probes are 18 and 14 bases in length and hybridize to the 16S rRNA of *H. influenzae* in the region corresponding to bases 837–855 and 1255–1269 of *E. coli*, respectively. To demonstrate the reactivity and specificity of the probes for *H. influenzae*, they were used in a hybridization assay. The probes were first synthesized with a non-nucleotide linker then labelled with a chemiluminescent acridinium ester as described in EPO Patent Application No. PCT/US88/03361 entitled "Acridinium Ester Labeling and Purification of Nucleotide Probes" filed Oct. 5, 1988. The acridinium ester (AE) attached to hybridized probe is relatively protected, while the acridinium ester attached to unhybridized probe is rendered non-chemiluminescent under mild alkaline conditions. Thus, it is possible to assay for hybridization of acridinium ester-labelled probe by incubation with an alkaline buffer, followed by detection of chemiluminescence in a luminometer. Results are expressed in Relative Light Units ("RLU"), the quantity of photons emitted by the labelled-probe measured by the luminometer. The conditions of hybridization, hydrolysis, and detection are described in Arnold, et al. (Clin. Chem. 35:1588–1594, 1989). The hybridization conditions described therein are a temperature of 60° C. in 0.1M lithium succinate buffer containing 10% lithium lauryl sulfate.

Nucleic acid hybridization was enhanced by the use of "Helper Probes" as disclosed in Hogan et al., U.S. patent application Ser. No. 124,975 entitled "Means and Methods for Enhancing Nucleic Acid Hybridization," allowed Dec. 17, 1990. RNA was hybridized to a mix of the two acridinium ester-labeled probes in the presence of unlabelled "Helper Probe" oligonucleotides complementary to the target RNA of sequence (SEQ ID NO: 3) 5'-CAAC-CCCCAAAT CGACAGCGTTTACAGCGTGG-3', (SEQ ID NO: 4) GCCGTACTCCCCAGGCGGTCGATT TAT-CACGTTAGCTACG-3', (SEQ ID NO: 5) 5'-CCTCTG-TATACGCCATTGTAGCACGTG TGTAGC-3', and (SEQ ID NO: 6) 5'-CCGGACTTAGACGTACTTTATGAGAT-TCGCTCC ACC T-3'. The Tms as determined by the Hybridization Protection Assay under these conditions were 66° C. and 64° C. for the two probes.

In the following experiment, RNA released from one colony or >$10^8$ cells was assayed. RLU values greater than 50,000 RLU were considered a positive reaction.

TABLE I

| Target | ATCC # | RLU value |
|---|---|---|
| Haemophilus aphrophilus | 33389 | 1,215 |
| Haemophilus ducreyi | 27422 | 1,772 |
| Haemophilus haemolyticus | 33390 | 1,370 |
| Haemophilus influenzae | 33391 | 208,755 |
| Haemophilus influenzae A | 9006 | 528,759 |
| Haemophilus influenzae aegyptius | 11116 | 803,094 |
| Haemophilus influenzae B | 33533 | 445,508 |
| Haemophilus influenzae C | 9007 | 280,656 |
| Haemophilus influenzae D | 9008 | 85,337 |
| Haemophilus influenzae E | 8142 | 511,100 |
| Haemophilus influenzae F | 9833 | 499,066 |
| Haemophilus parahaemolyticus | 10014 | 1,815 |
| Haemophilus parainfluenzae | 7901 | 1,932 |
| Haemophilus paraphrophilus | 29241 | 1,203 |

The following experiment shows that the probes do not cross react with bacteria from a wide phylogenetic cross section.

TABLE II

| Target | ATCC # | RLU value |
|---|---|---|
| Acinetobacter calcoaceticus | 33604 | 1,212 |
| Bacillus subtilis | 6051 | 818 |
| Bacteroides fragiles | 23745 | 800 |
| Branhamella catarrhalis | 25238 | 525 |
| Campylobacter jejune | 33560 | 1,215 |
| Candida albicans | 18804 | 633 |
| Chromobacterium violaceum | 29094 | 1,093 |
| Clostridium perfringens | 13124 | 1,130 |
| Deinococcus radiodurans | 35073 | 868 |
| Derxia gummosa | 15994 | 5,773 |
| Pseudomonas aeruginosa | 25330 | 839 |
| Rahnella aquaticus | 33071 | 762 |
| Rhodospirillum rubrum | 11170 | 821 |
| Staphylococcus aureus | 12598 | 646 |
| Staphylococcus epidermidis | 12228 | 528 |
| Streptococcus agalactiae | 13813 | 581 |
| Streptococcus mitis | 9811 | 535 |
| Streptococcus pneumoniae | 6303 | 465 |
| Vibrio parahaemolyticus | 17801 | 866 |
| Yersinia enterocolitica | 9610 | 1,028 |

The above data confirm that the novel probes herein disclosed and claimed are capable of distinguishing *Haemophilus influenzae* from its known nearest phylogenetic neighbors.

We claim:

1. An oligonucleotide hybridization assay probe able to specifically detect *Haemophilus influenzae* consisting of a nucleotide sequence of 10 to 100 bases sufficiently complementary to rRNA of said *Haemophilus influenzae* in a region corresponding to bases 837–854 of *E. coli* 16S rRNA, to form a first detectable duplex under selective hybridization conditions comprising 60° C. in 0.1M lithium succinate buffer containing lithium lauryl sulfate, wherein said oligonucleotide does not form a second detectable duplex under said conditions with nucleic acid from *Haemophilus aphrophilus, Haemophilus ducreyi, Haemophilus haemolyticus, Haemophilus parahaemolyticus, Haemophilus parainfluenzae,* or *Haemophilus paraphrophilus*.

2. The probe of claim 1, wherein said oligonucleotide contains an acridinium ester label.

3. The probe of claim 1, wherein said oligonucleotide contains a 10 base pair region perfectly complementary to 10 bases present in a nucleotide sequence selected from the group consisting of: 5' GGCGCCAGAGTTAAACCC 3' (SEQ ID NO: 1) and the RNA complement of SEQ ID NO: 1.

4. An oligonucleotide hybridization assay probe able to specifically detect of *Haemophilus influenzae* comprising a nucleotide sequence about 18 bases in length selected from the group consisting of:

5' GGCGCCAGAGTTAAACCC 3' (SEQ ID NO: 1), the DNA complement of SEQ ID NO: 1, the RNA complement of SEQ ID NO: 1, and the RNA complement of the DNA complement of SEQ ID NO: 1 wherein said oligonucleotide can hybridize to *Haemophilus influenzae* nucleic acid under stringent hybridization assay conditions to form a first detectable duplex, but does not hybridize to nucleic acid from *Haemophilus aphrophilus, Haemophilus haemolyticus, Haemophilus parahaemolyticus, Haemophilus parainfluenzae,* or *Haemophilus paraphrophilus* to form a second detectable duplex under said conditions.

5. The probe of claim 4, wherein said oligonucleotide contains an acridinium ester label.

6. An oligonucleotide hybridization assay probe able to specifically detect *Haemophilus influenzae* which is 18 to 100 bases in length comprising nucleotide sequence selected from the group consisting of:

5' GGCGCCAGAGTTAAACCC 3' (SEQ ID NO: 1), the DNA complement of SEQ ID NO: 1, the RNA complement of SEQ ID NO: 1, and the RNA complement of the DNA complement of SEQ ID NO: 1 wherein said oligonucleotide can hybridize to *Haemophilus influenzae* nucleic acid under stringent hybridization assay conditions to form a first detectable duplex, but does not hybridize to nucleic acid from *Haemophilus aphrophilus, Haemophilus haemolyticus, Haemophilus parahaemolyticus, Haemophilus parainfluenzae,* or *Haemophilus paraphrophilus* to form a second detectable duplex under said conditions.

7. The probe of claim 6, wherein said oligonucleotide is 18–50 nucleotides in length.

8. The probe of claim 6, wherein said oligonucleotide consists of said nucleotide sequence.

9. The probe of claim 8, wherein said oligonucleotide contains an acridinium ester label.

10. A probe mix comprising:

an oligonucleotide hybridization assay probe 10 to 100 bases in length sufficiently complementary to rRNA of *Haemophilus influenzae* in the region corresponding to bases 837–854 of *E. coli* 16S rRNA, and at least one helper probe; wherein said helper probe is selected from the group consisting of oligonucleotides comprising the sequence 5' CAACCCCCAAATCGACAGCGTTTACAGCGTGG (SEQ ID NO: 3), and

5'           GCCGTACTCCCCAGGCGGTCGATTTATCACGTTAGCTACG (SEQ ID NO: 4).

11. The probe mix of claim 10, wherein said hybridization assay probe comprises a nucleotide sequence about 18 bases in length selected from the group consisting of:

5' GGCGCCAGAGTTAAACCC 3' (SEQ ID NO: 1), the DNA complement of SEQ ID NO: 1, the RNA complement of SEQ ID NO: 1, and the RNA complement of the DNA complement of SEQ ID NO: 1.

12. The probe mix of claim 10, wherein said probe is 18 to 100 bases in length comprising a nucleotide sequence selected from the group consisting of:

5' GGCGCCAGAGTTAAACCC 3' (SEQ ID NO: 1), the DNA complement of SEQ ID NO: 1, the RNA complement of SEQ ID NO: 1, and the RNA complement of the DNA complement of SEQ ID NO: 1.

13. The probe mix of claim 12, wherein said hybridization assay probe consists of said hybridization assay probe nucleotide sequence and said helper probe consists of said helper probe nucleotide sequence.

14. A method for detecting the presence of *Haemophilus influenzae* nucleic acid in a sample comprising the steps of:

a) contacting said nucleic acid under stringent hybridization assay conditions with a nucleic acid hybridization assay probe able to hybridize to rRNA from *Haemophilus influenzae* in a region corresponding to bases 837–854 of *E. coli* 16S rRNA to form a first detectable duplex under stringent hybridization conditions, wherein said probe does not form a second detectable duplex with nucleic acid from *Haemophilus aphrophilus, Haemophilus ducreyi, Haemophilus haemolyticus, Haemophilus parahaemolyticus, Haemophilus parainfluenzae,* or *Haemophilus paraphrophilus* under said conditions;

b) measuring the presence or amount of said first detectable duplex.

15. The method of claim 14, wherein said probe contains a 10 base pair region perfectly complementary to 10 bases present in a nucleotide sequence selected from the group consisting of:

5' GGCGCCAGAGTTAAACCC 3' (SEQ ID NO: 1) and

5' GGGUUUAACUCUGGCGCC 3' (SEQ ID NO: 8).

16. The method of claim 14, wherein said probe comprises a nucleotide sequence about 18 bases in length selected from the group consisting of:

5' GGCGCCAGAGTTAAACCC 3' (SEQ ID NO: 1), the DNA complement of SEQ ID NO: 1, the RNA complement of SEQ ID NO: 1, and the RNA complement of the DNA complement of SEQ ID NO: 1.

17. The method of claim 14, wherein said probe is 18 to 100 bases in length comprising a nucleotide sequence selected from the group consisting of:

5' GGCGCCAGAGTTAAACCC 3' (SEQ ID NO: 1), the DNA complement of SEQ ID NO: 1, the RNA complement of SEQ ID NO: 1, and the RNA complement of the DNA complement of SEQ ID NO: 1.

18. The method of claim 17, wherein said probe is 18 to 50 bases in length.

19. The method of claim 18, wherein said probe consists of said nucleotide sequence.

* * * * *

UNITED STATES PATENT AND TRADEMARK OFFICE
CERTIFICATE OF CORRECTION

PATENT NO. : 5,472,843
DATED : December 5, 1995
INVENTOR(S) : Curt Milliman

It is certified that error appears in the above-indentified patent and that said Letters Patent is hereby corrected as shown below:

| Col. | Line | |
|---|---|---|
| 10 | 11 | Change "27422" to --33921--. |
| 13 | 13 | Replace "rRNA" with --rRNA, or a nucleotide polymer complementary thereto,-- |
| 13 | 14 | After "rRNA," insert --or a nucleotide polymer complementary thereto,-- |
| 14 | 13 | Replace "rRNA" with --rRNA, or a nucleotide polymer complementary thereto,-- |
| 14 | 15 | After "rRNA,", insert --or a nucleotide polymer complementary thereto,-- |
| 14 | 47 | Replace "rRNA" with --rRNA, or a nucleotide polymer complementary thereto,-- |
| 14 | 49 | Replace "rRNA" with --rRNA, or a nucleotide polymer complementary thereto,-- |
| 14 | 64 | Delete "5' GGGUUUAACUCUGGCGCC3' (Seq ID NO:8)" and insert --the RNA complement of SEQ ID NO:1--. |

Signed and Sealed this

Twenty-first Day of April, 1998

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 18 bases
( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:1:

GGCGCCAGAG TTAAACCC 18

( 2 ) INFORMATION FOR SEQ ID NO:2:

( i ) SEQUENCE CHARACTERISTICS:
( A ) LENGTH: 14 bases
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

CGCAGCTTCG CTTC 14

( 2 ) INFORMATION FOR SEQ ID NO:3:

( i ) SEQUENCE CHARACTERISTICS:
( A ) LENGTH: 32 bases
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

CAACCCCCAA ATCGACAGCG TTTACAGCGT GG 32

( 2 ) INFORMATION FOR SEQ ID NO:4:

( i ) SEQUENCE CHARACTERISTICS:
( A ) LENGTH: 40 bases
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

GCCGTACTCC CCAGGCGGTC GATTTATCAC GTTAGCTACG 40

( 2 ) INFORMATION FOR SEQ ID NO:5:

( i ) SEQUENCE CHARACTERISTICS:
( A ) LENGTH: 33 bases
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:5:

CCTCTGTATA CGCCATTGTA GCACGTGTGT AGC 33

( 2 ) INFORMATION FOR SEQ ID NO:6:

( i ) SEQUENCE CHARACTERISTICS:
( A ) LENGTH: 37 bases
( B ) TYPE: nucleic acid
( C ) STRANDEDNESS: single
( D ) TOPOLOGY: linear ( i i ) MOLECULE TYPE: DNA (xi) SEQUENCE DESCRIPTION: SEQ ID NO:6:

CCGGACTTAG ACGTACTTTA TGAGATTCGC TCCACCT    37